(12) United States Patent
Livneh

(10) Patent No.: US 7,871,423 B2
(45) Date of Patent: Jan. 18, 2011

(54) FORCEPS FOR PERFORMING ENDOSCOPIC OR ARTHROSCOPIC SURGERY

(75) Inventor: Steve Livneh, Amherstburg (CA)

(73) Assignee: Bovie Medical Corporation, St. Petersburg, FL (US)

( * ) Notice: Subject to any disclaimer, the term of this patent is extended or adjusted under 35 U.S.C. 154(b) by 1295 days.

(21) Appl. No.: 11/380,797

(22) Filed: Apr. 28, 2006

(65) Prior Publication Data

US 2006/0259070 A1 Nov. 16, 2006

Related U.S. Application Data

(60) Provisional application No. 60/676,645, filed on Apr. 29, 2005, provisional application No. 60/717,074, filed on Sep. 14, 2005.

(51) Int. Cl.
*A61B 17/00* (2006.01)

(52) U.S. Cl. ....................................... 606/205

(58) Field of Classification Search ................ 403/84, 403/92–95, 109.1–109.8, 322.2, 325, 326, 403/327; 606/48, 50, 51, 170, 205
See application file for complete search history.

(56) References Cited

U.S. PATENT DOCUMENTS

| | | | |
|---|---|---|---|
| 4,043,343 A | | 8/1977 | Williams |
| 4,569,131 A | * | 2/1986 | Falk et al. ..................... 30/251 |
| 4,944,093 A | * | 7/1990 | Falk ............................. 30/251 |
| 5,395,375 A | | 3/1995 | Turkel et al. |
| 5,562,655 A | | 10/1996 | Mittelstadt et al. |
| 5,567,080 A | * | 10/1996 | Sterlacci ................... 403/322.1 |
| 5,569,299 A | | 10/1996 | Dill et al. |
| 5,603,723 A | | 2/1997 | Aranyi et al. |
| 5,643,307 A | | 7/1997 | Turkel et al. |
| 5,649,955 A | | 7/1997 | Hashimoto et al. |
| 5,683,359 A | | 11/1997 | Farkas et al. |
| 5,718,714 A | * | 2/1998 | Livneh ........................ 606/205 |
| 5,741,285 A | | 4/1998 | McBrayer et al. |
| 5,810,879 A | | 9/1998 | deGillebon |
| 5,810,883 A | | 9/1998 | Lang |

(Continued)

FOREIGN PATENT DOCUMENTS

DE 197 13 067 A1 10/1998

OTHER PUBLICATIONS

PCT International Search Report for PCT/US2006/016519, mailed Oct. 30, 2006.

*Primary Examiner*—Todd E Manahan
*Assistant Examiner*—Christopher Schubert
(74) *Attorney, Agent, or Firm*—Howard & Howard Attorneys PLLC

(57) ABSTRACT

Forceps for performing endoscopic or arthroscopic surgery include a body assembly, a tube assembly, and a pair of handles that pivot with respect to the body. The tube assembly is removably attached to the body assembly. The tube assembly includes a hollow tube and a tip assembly. The tip assembly includes an electrode or a blade for performing the surgery. The tip assembly and the blade are connected to the body and the handles by a cable. As the handles pivot, the cable slides within the tube to move the blade. When a different tube assembly (i.e., a bipolar or a monopolar electrode) or another style of tip assembly are desired, the installed one is removed and replaced by a new tube assembly or tip assembly as desired.

22 Claims, 18 Drawing Sheets

U.S. PATENT DOCUMENTS

| | | |
|---|---|---|
| 6,030,409 A | 2/2000 | Lang |
| RE36,666 E | 4/2000 | Honkanen et al. |
| 6,077,290 A | 6/2000 | Marini |
| 6,117,158 A | 9/2000 | Measamer et al. |
| 6,280,458 B1 | 8/2001 | Boche et al. |
| H2037 H | 7/2002 | Yates et al. |
| 6,682,548 B2 | 1/2004 | Lang et al. |
| 7,395,830 B2 * | 7/2008 | Seo ............................ 135/140 |
| 2004/0098038 A1 | 5/2004 | Lang et al. |
| 2004/0220601 A1 | 11/2004 | Lang et al. |
| 2004/0230221 A1 | 11/2004 | Gadberry et al. |
| 2005/0245923 A1 | 11/2005 | Christopherson et al. |

* cited by examiner

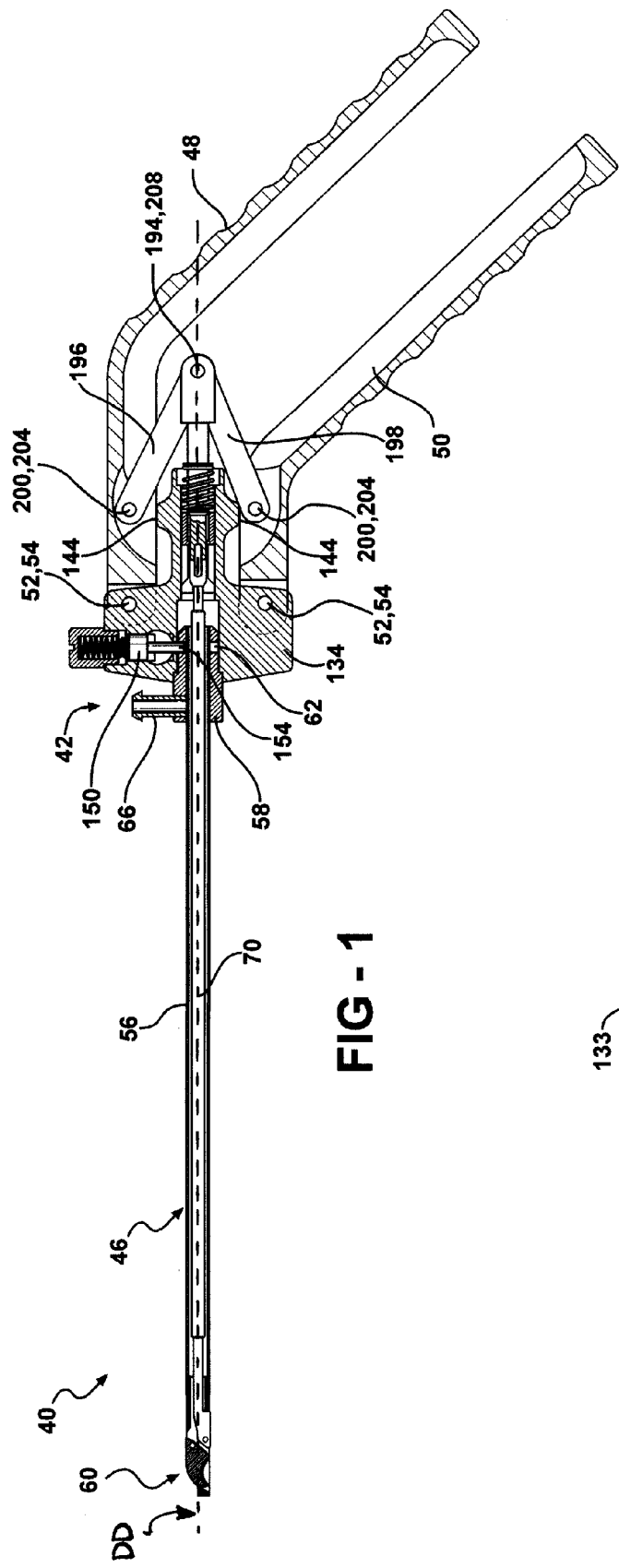
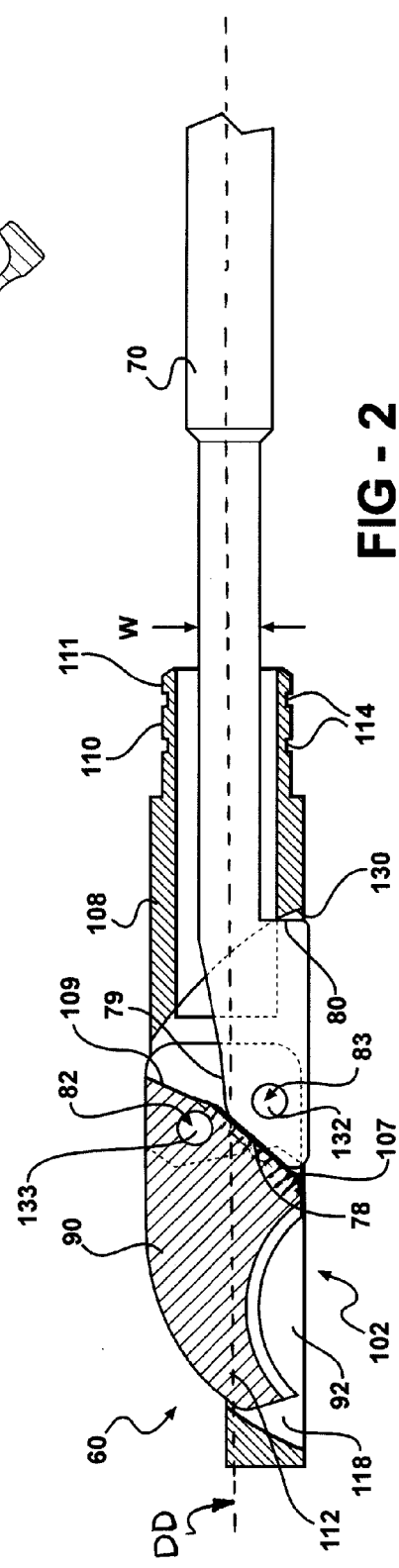
FIG - 1
FIG - 2

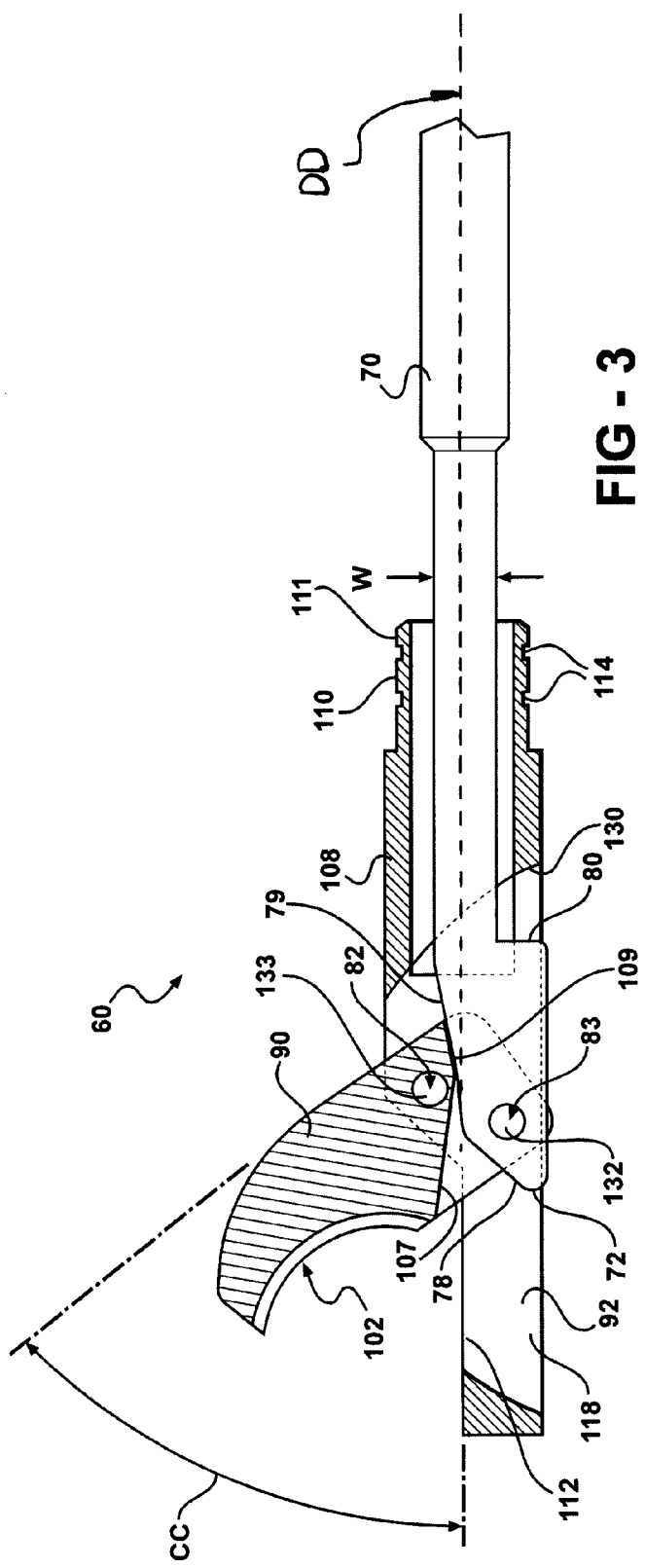
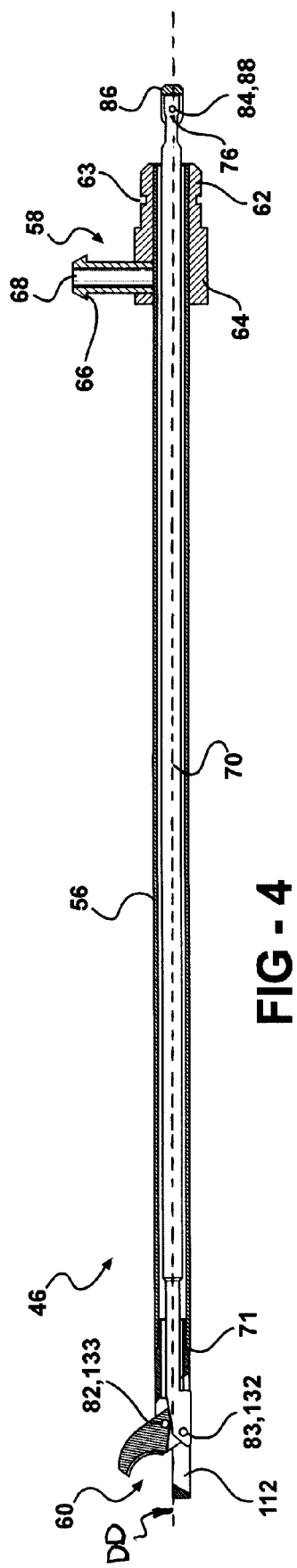
FIG - 3
FIG - 4

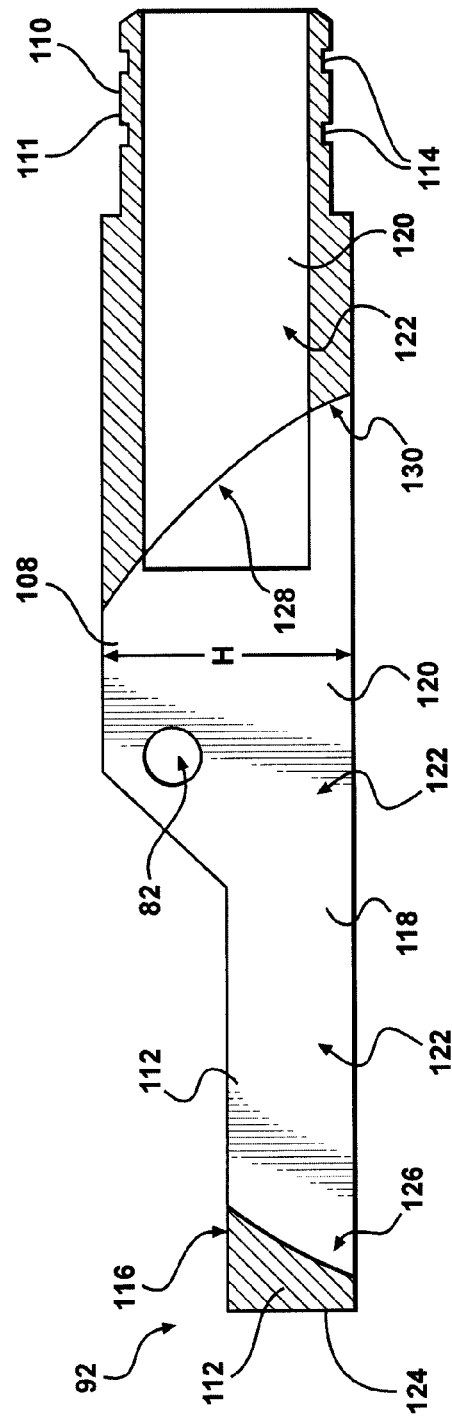

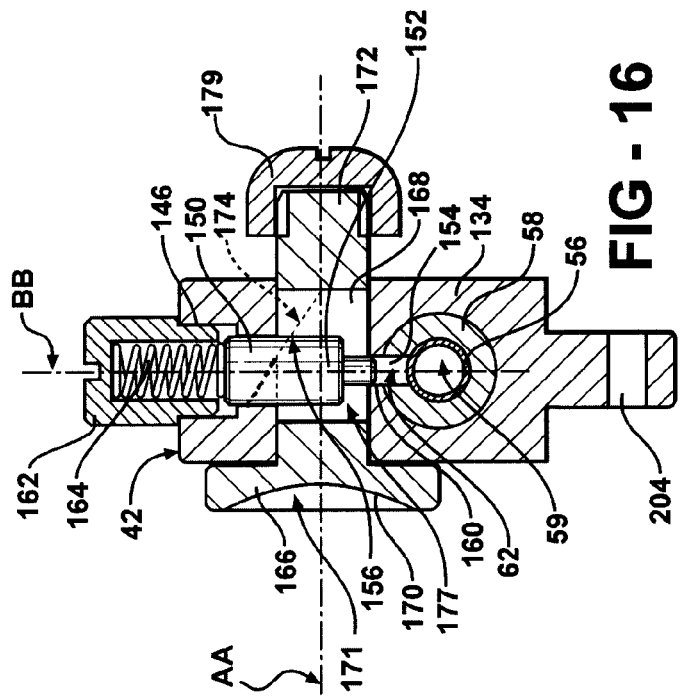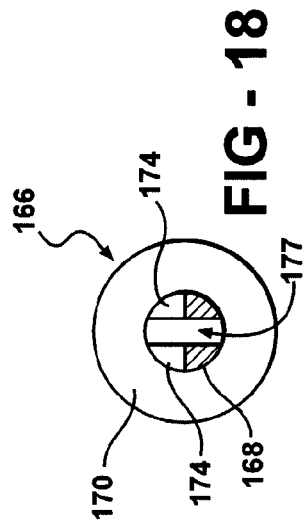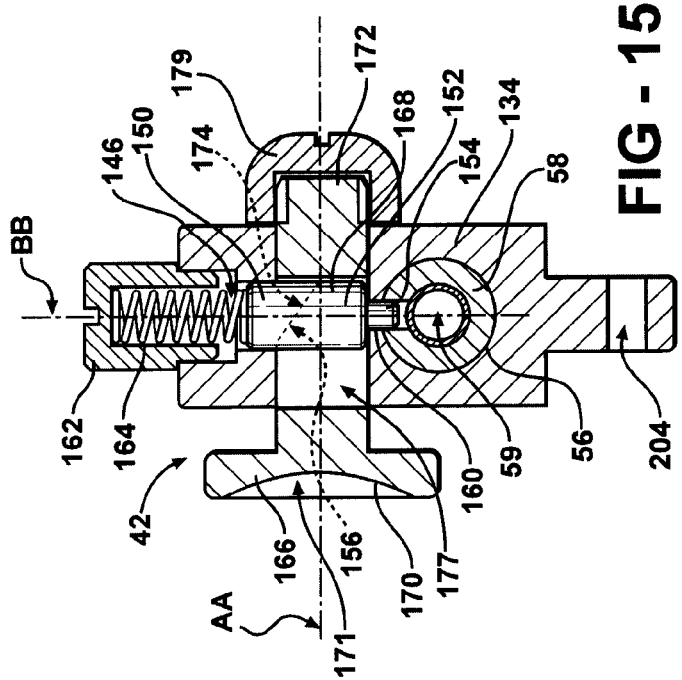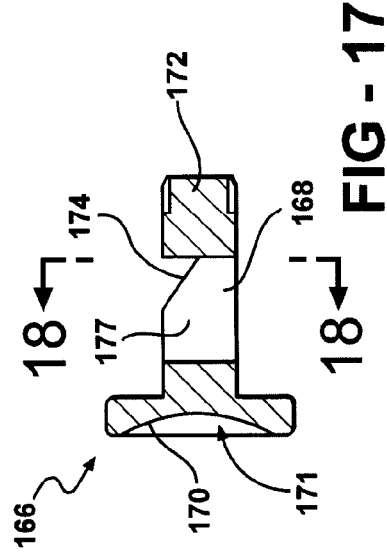

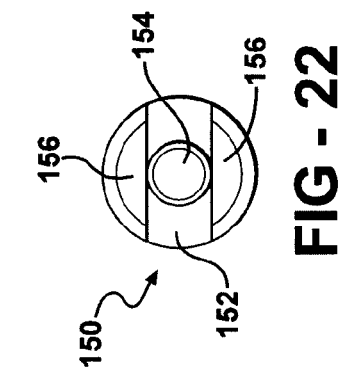 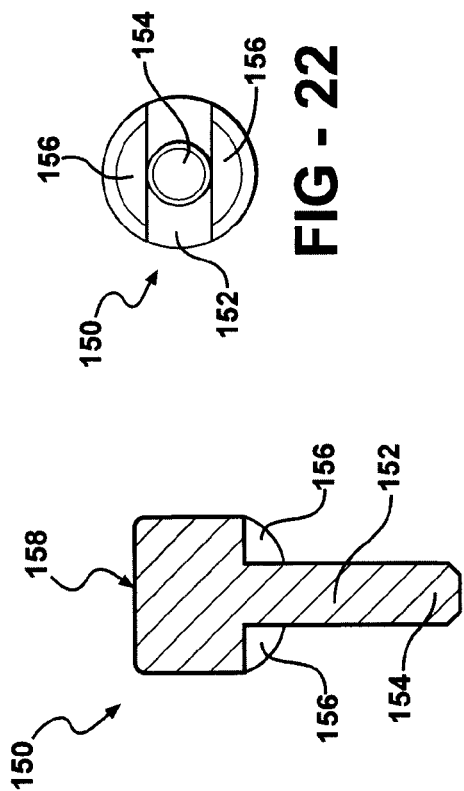 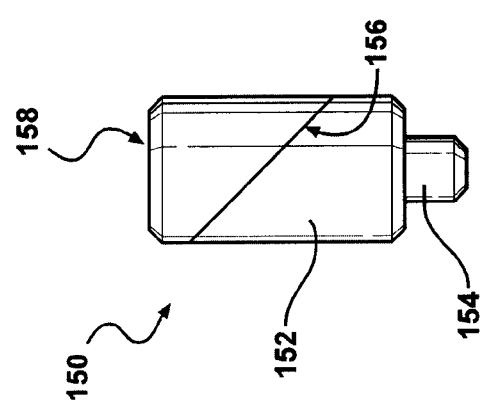 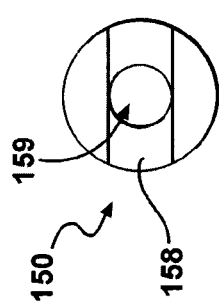 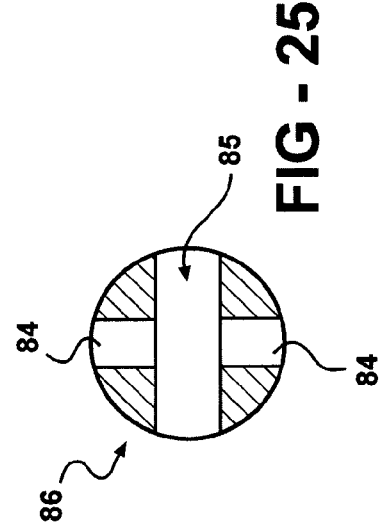 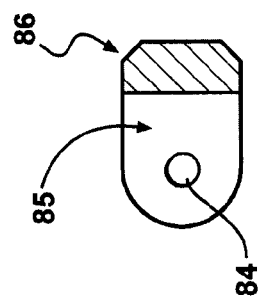 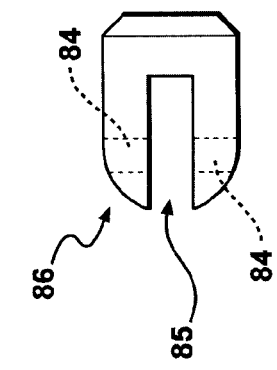

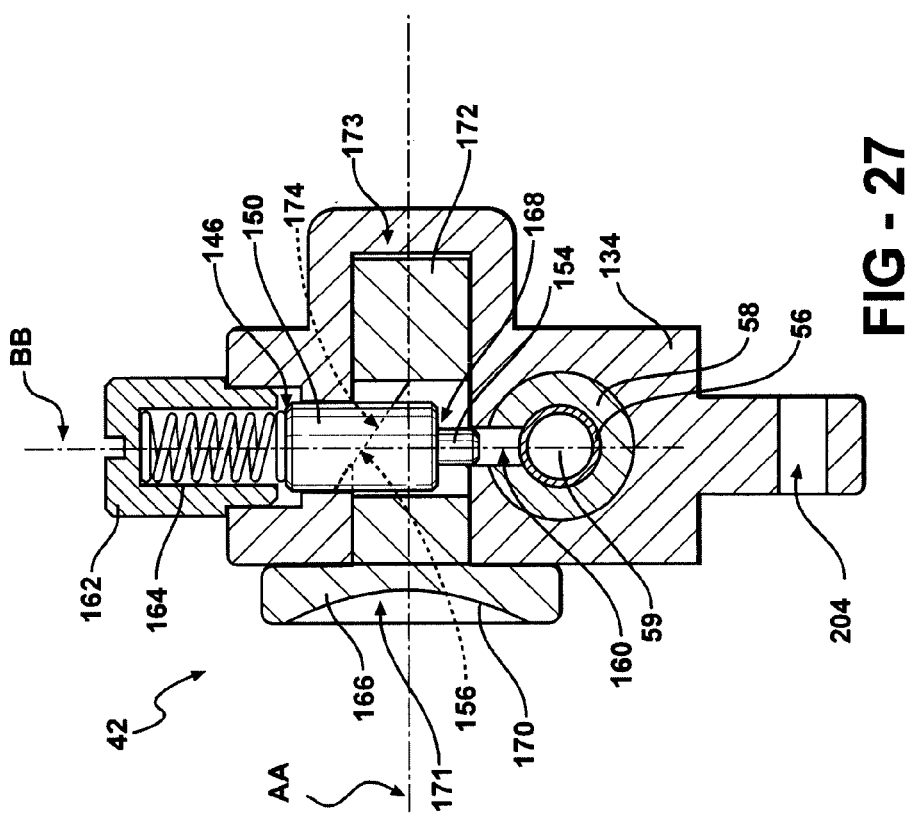
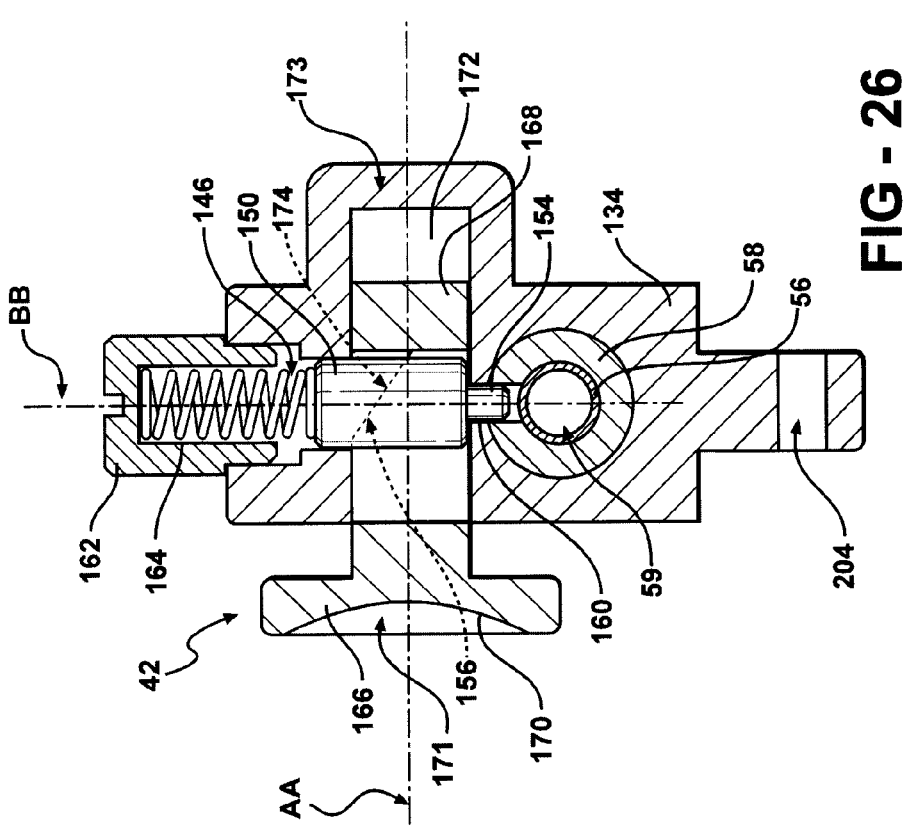

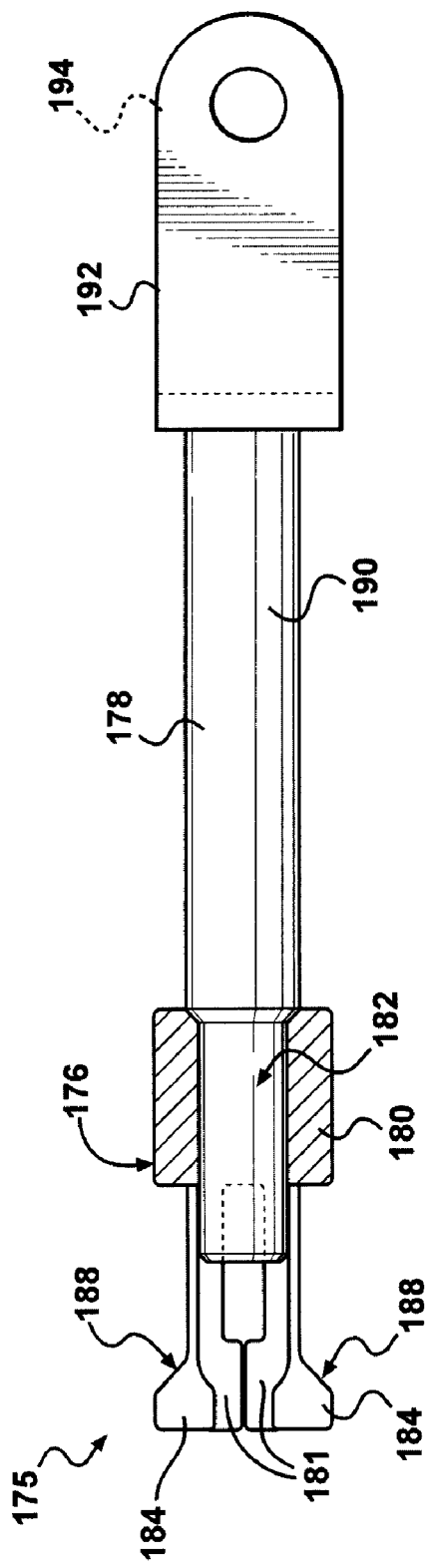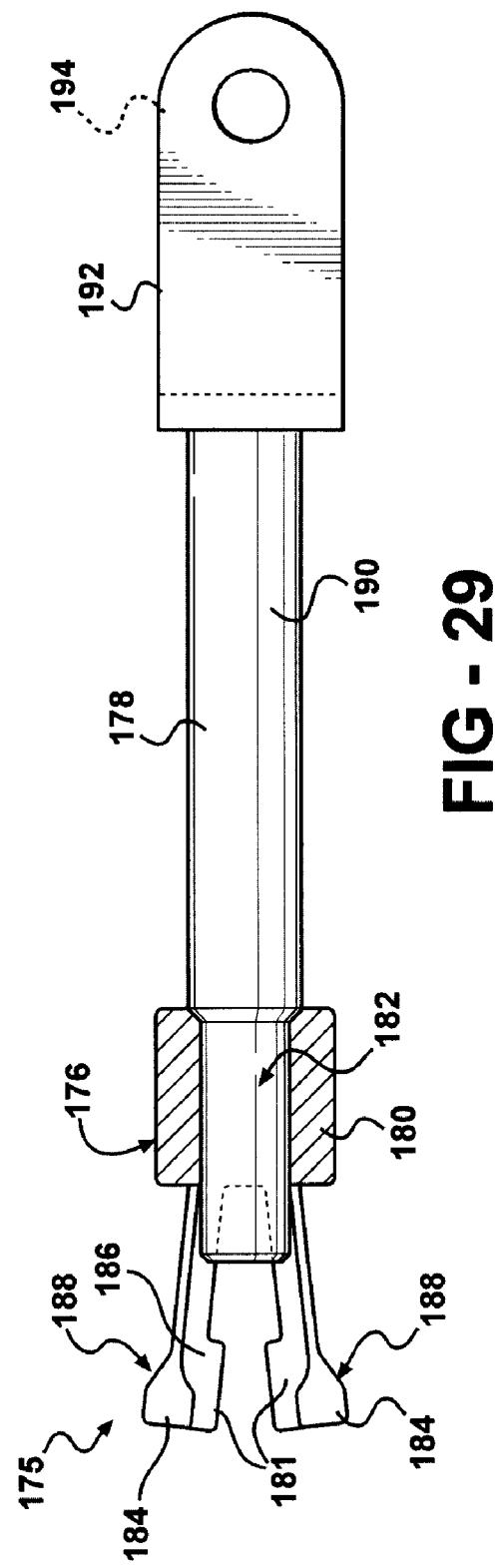

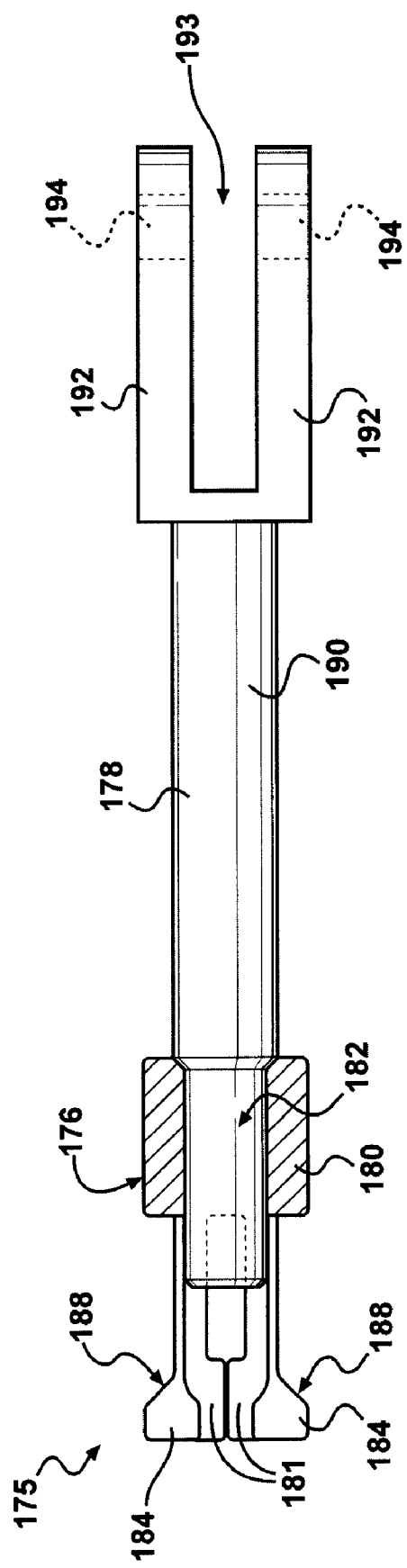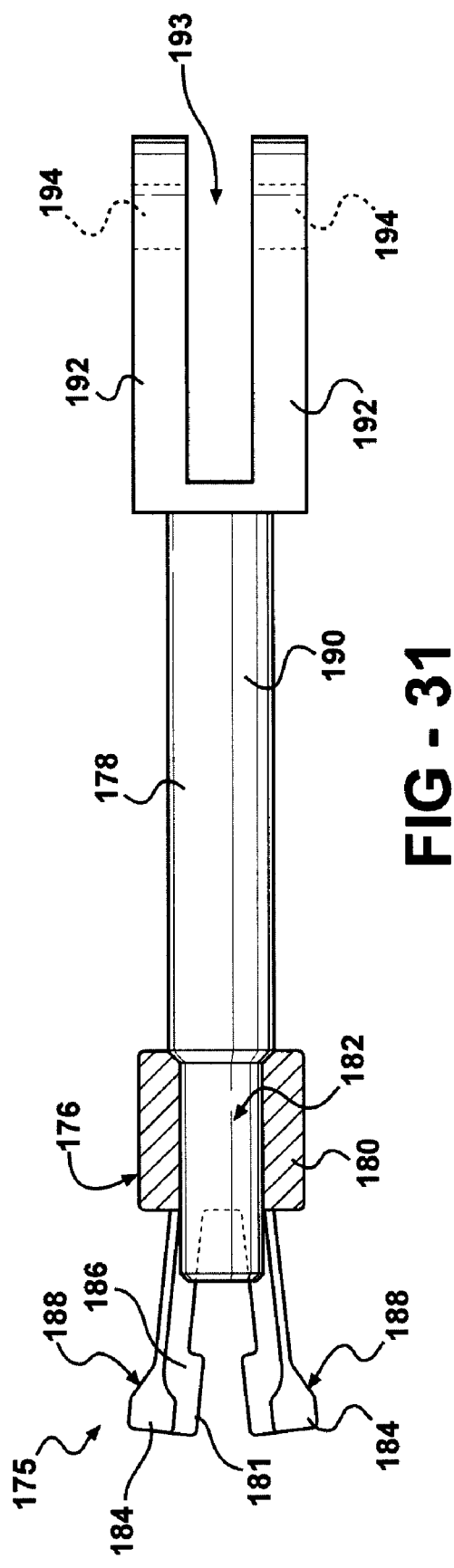

US 7,871,423 B2

FORCEPS FOR PERFORMING ENDOSCOPIC OR ARTHROSCOPIC SURGERY

CROSS REFERENCE TO RELATED APPLICATION

This application claims the benefit of U.S. Provisional Patent Application Ser. Nos. 60/676,645 and 60/717,074, which are hereby incorporated by reference.

BACKGROUND OF THE INVENTION

Today's endoscopic and arthroscopic surgical instruments encompass a multitude of different designs. While all may be designed to serve the same function, for example, each one may be shaped differently to provide the surgeon better access to perform the procedure. For example, a pair of forceps may include a tube that extends from a pair of handles. A blade is disposed at an end to the tube for performing the surgery. The tube, near the blade in one pair of forceps is bent upward to provide the surgeon with the required access in the patient to make a first cut. However, if the surgeon needs to perform a second cut, on the same patient, but in a different position, the surgeon must get a different pair of forceps where the tube is bent to a different orientation.

Based on the above, it is easy to relate to today's realities of the operating room where a large inventory of specific instruments must be kept in an inventory at a high cost. Managing and maintaining this inventory is costly and complex. Lack of flexibility among the instruments are a direct added cost to each surgery, while maintaining the different variety of instruments necessitates trained personnel and sterilization facilities and capabilities.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is cross-sectional side view of forceps;

FIG. 2 is cross-sectional side view of a tip assembly showing a cable in an aft position with a blade inside a tip of the tip assembly in a closed position;

FIG. 3 is a cross-sectional side view of the tip assembly showing the cable in a forward position with the blade in an open position;

FIG. 4 is a cross-sectional side view of a tube assembly with the blade in the open position;

FIG. 8 is cross-sectional side view of the tip;

FIG. 9 is a bottom view of the tip;

FIG. 15 is a cross-sectional front view of the body assembly showing a lock engaging an adapter of the tube assembly;

FIG. 16 is a cross-sectional front view of the body assembly showing a plunger depressed and the lock disengaged from the adapter of the tube assembly;

FIG. 17 is a cross-sectional side view of the plunger;

FIG. 18 is a cross-sectional front view of the plunger taken along line A-A of FIG. 17;

FIG. 19 is a top view of the lock;

FIG. 20 is a side view of the lock;

FIG. 21 is a cross-sectional view of the lock;

FIG. 22 is a bottom view of the lock;

FIG. 23 is a top view of the cable retainer;

FIG. 24 is a cross-sectional side view of cable retainer;

FIG. 25 is an end view of cable retainer;

FIG. 26 is a cross-sectional front view of an alternative body assembly showing a plunger in a relaxed position and the lock engaged with the adapter of the tube assembly;

FIG. 27 is a cross-sectional front view of the body assembly in FIG. 26 showing the plunger depressed and the lock disengaged from the adapter of the tube assembly;

FIG. 28 is a partial cross-sectional side view of a grabbing mechanism assembly illustrating jaws of a collet in a closed position;

FIG. 29 is a partial cross-sectional side view of the grabbing mechanism assembly illustrating the jaws of the collet in the open position;

FIG. 30 is a partial cross-sectional top view of the grabbing mechanism assembly illustrating the jaws of the collet in the closed position;

FIG. 31 is a partial cross-sectional top view of the grabbing mechanism assembly illustrating the jaws of the collet in the open position;

DETAILED DESCRIPTION OF THE PREFERRED EMBODIMENT

Figure 5:
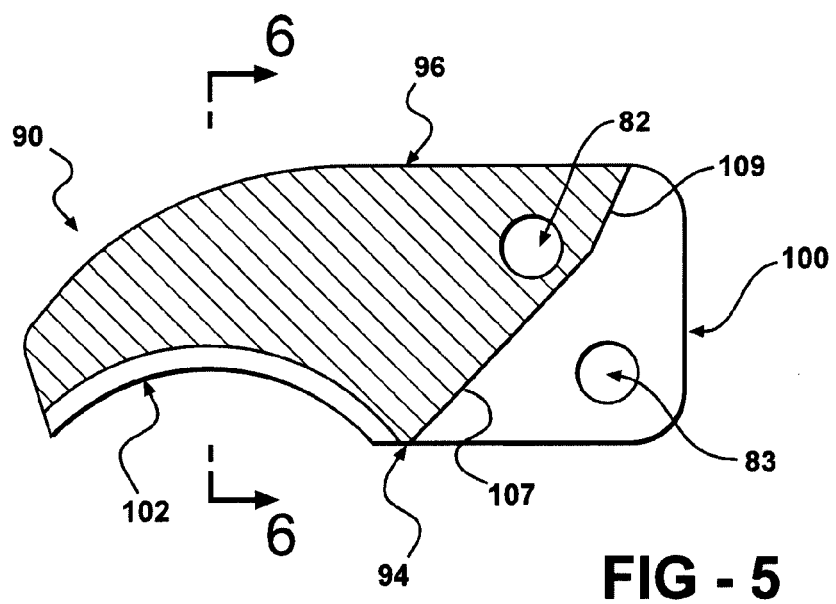
FIG. 5 is a cross-sectional side view of the blade.

Referring to the Figures, wherein like numerals indicate like parts throughout the several views, forceps are generally shown at 40. Forceps 40 are used for performing various procedures during endoscopic or laparoscopic types of surgery. A common type of procedure is cutting. However, they can be used to perform other types of procedures such as grasping, manipulating, or ablating, for example.

The forceps 40 include a body assembly 42, a tube assembly 46, and a pair of opposing handles 48, 50. The handles 48, 50 include an upper handle 48 and a lower handle 50. The handles 48, 50 are pivotally connected to the body assembly 42. A handle screw 52 attaches each handle to the body assembly 42 but allows the handles 48, 50 to pivot. Teflon washers 54 may be interposed between each of the handles 48, 50 and the body assembly 42 for reducing friction when pivoting each handle 48, 50 with respect to the body assembly 42.

The tube assembly 46, shown in FIG. 4, includes a hollow tube 56 extending between an adapter 58 and a tip assembly 60 along a tube axis DD. The adapter 58 encircles the tube 56 and defines a plurality of locking holes or indentations 62 in grooves 63 encircling the adapter 58. The tube 56 and the adapter 58 each define a hollow interior 59. A flushing port 66 is formed in and extends from the adapter 58. The flushing port 66 defines a duct 68 into the hollow interior 59 of the adapter 58 for flushing the tube assembly 46. A cable 70 is connected to the blade 90 via pin 83 and extends through the tube assembly 46 and out beyond the adapter 58.

Figure 14:
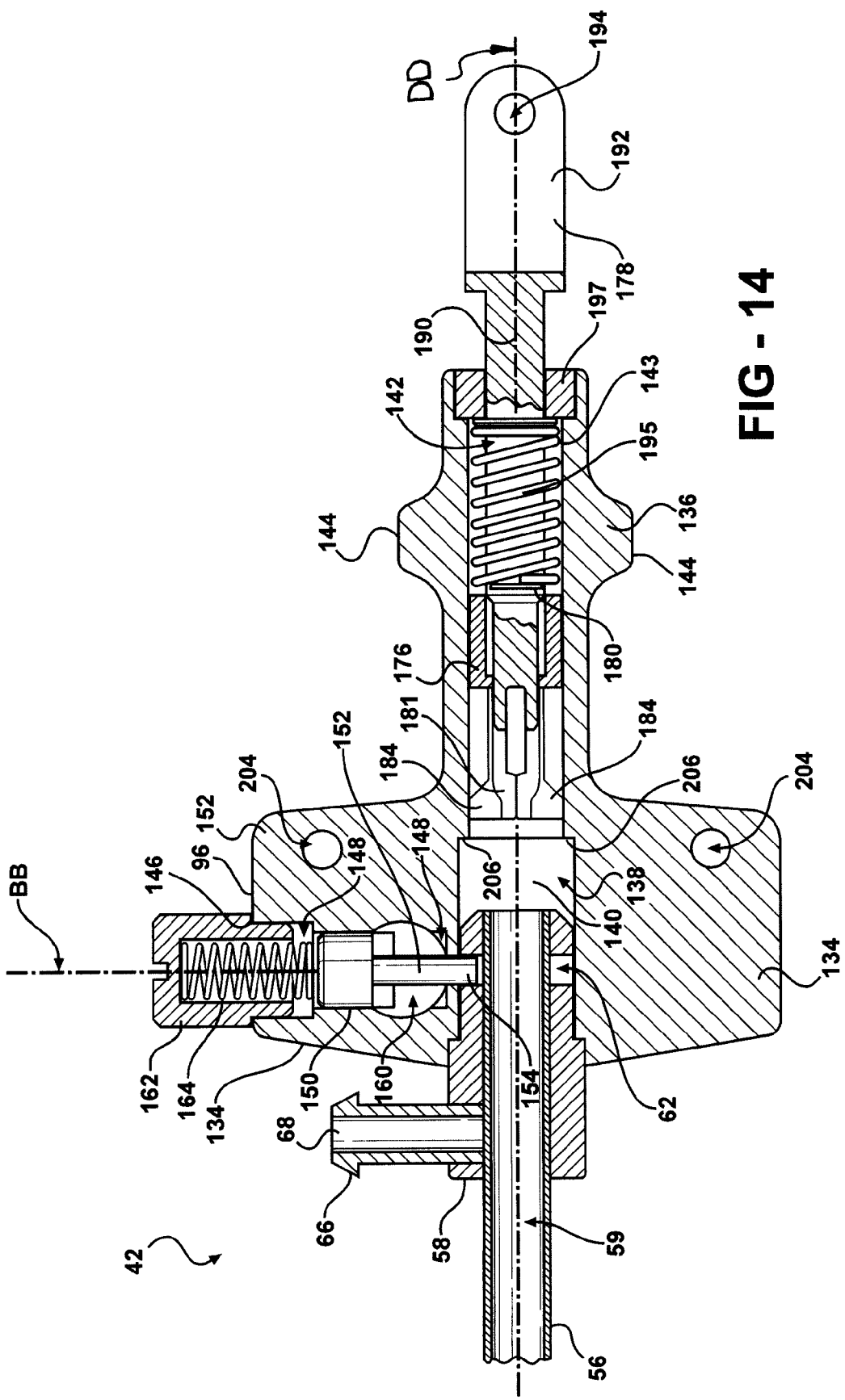
FIG. 14 is a cross-sectional side view of a body assembly.

The tip assembly 60, shown in FIGS. 2 and 3, extends from a distal end 71 of the tube 56 for performing the cutting procedures. The cable 70, shown in FIGS. 10-13, extends through the tube 56 and interconnects the tip assembly 60 to the handles 48, 50. The cable 70 is flat or having at least flat end portions, having a thickness T, and extending between a blade end 74 and a cable end 76. The blade end 74 is disposed in the body 134 proximate the tip assembly 60, as shown in FIG. 14. The cable end 76 is disposed in the body assembly 42, proximate the handles 48, 50. The cable 70 tapers to a reduced width W before each of the blade end 74 and the cable end 76. The blade end 74 extends from the reduced width W and has a generally trapezoidal shape with a front sloping edge 78 and a top edge 79. The blade end 74 defines a shoulder 80, opposite the front sloping edge 78 and adjacent the reduced width W. The blade end 74 defines a tip pinhole 83. The cable end 76 has a generally rectangular shape that extends from the reduced width W. The cable end 76 defines a shear pinhole 84. A cable retainer 86, for mounting to the cable end 76, is generally bullet shaped with a round cross-section, as shown in FIGS. 23-25. The cable retainer 86 defines a shear pin hole 84. A slot 85 is defined in the cable retainer 86 that is at least equal in size to the thickness T of the cable 70. The cable retainer 86 also defines a shear pinhole 84 that extends through the slot 85. The thickness T of the cable end 76 is inserted into the slot 85 and the shear pin holes 84 are aligned along the same axis. A shear pin 88 is inserted through the shear pin holes 84 to retain the cable retainer 86 onto the cable end 76.

Figure 6:
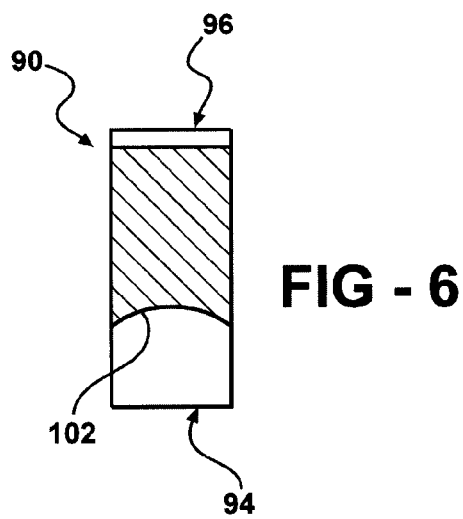
FIG. 6 is cross-sectional front view of the blade taken along section A-A of FIG. 5.
Figure 7:
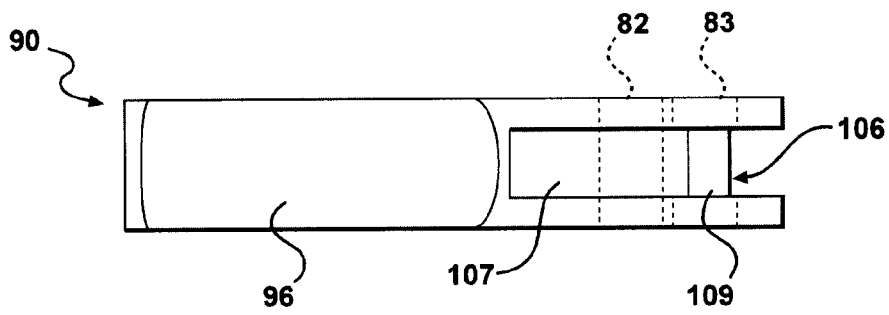
FIG. 7 is a bottom view of the blade.
Figure 10:
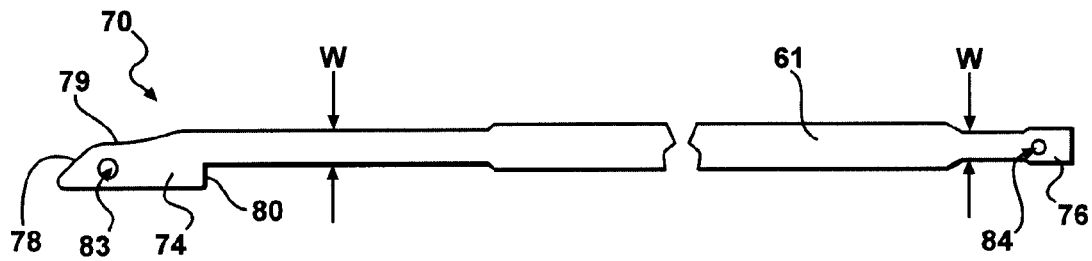
FIG. 10 is a side view of the cable.
Figure 11:
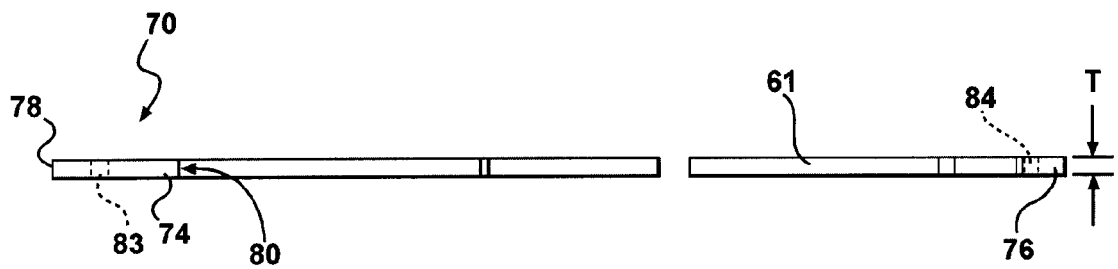
FIG. 11 is a bottom view of the cable.
Figure 12:
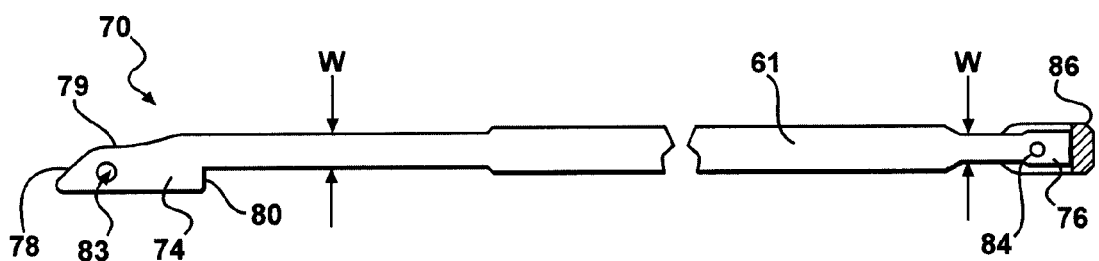
FIG. 12 is a side view of the cable showing a cable retainer assembled to a cable end of the cable.
Figure 13:
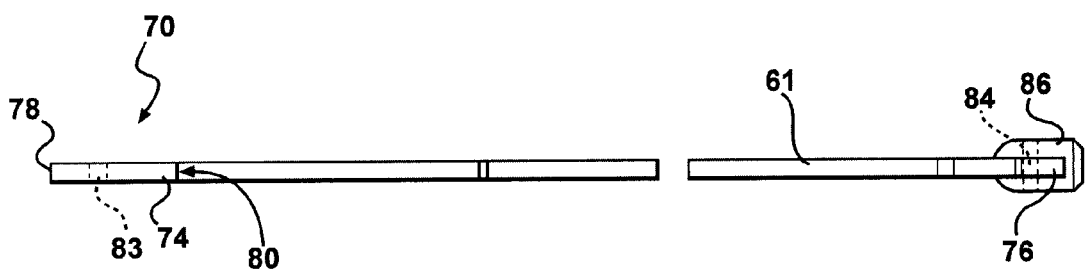
FIG. 13 is a bottom view of the cable showing the cable retainer assembled to the cable end of the cable.

The tip assembly 60 includes a blade 90 and a tip 92. The blade 90, shown in FIGS. 5-7, is a single-acting blade 90 that pivots relative to the tip 92 to perform the cutting procedure. However, the present invention is not limited to a single-acting blade 90, but may also be double-acting blades 90, or even jaws, where the elements pivot relative to one another. The blade 90 is flat and is generally rectangular in shape. The blade 90 is bounded by a bottom surface 94, an upper surface 96, a front 98, and a rear 100. The bottom surface 94 of the blade 90 defines a concave cutting region 102. The upper surface 96 of the blade 90, opposite the bottom surface 94 and the cutting region 102, is rounded toward a front 98 of the blade 90. The rounded upper surface 96 and the concave cutting region 102 give the blade 90 the appearance of a "claw". The rear 100 of the blade 90 defines a blade cavity 106 that extends into the blade 90. The blade 90 also defines a tip pin hole 82 and a cable pin hole 83 extending through the blade 90 and the blade cavity 106. Finally, the blade 90 includes a first blade stop 107 and a second blade stop 109 extending between the bottom surface 94 and the upper surface 96.

Referring to FIGS. 8 and 9, a tip 92 includes a shaft 108 that extends between a cylindrical neck 110 and a cutting portion 112. The shaft 108 has a diameter H. The neck 110 has an external diameter D which is less than the diameter H of the shaft 108. The neck 110 defines at least one external circumferential grooves 114 that encircle the neck 110. The neck 110 is engaged when inserted into the distal end 71 of the tube 56 for retaining the tip assembly 60 to the tube 56. The neck 110 can be attached to the shaft 108 by brazing, laser welding, adhesives or soldering, for example. When the shaft 108 is soldered to the tube 56, a soldering compound is applied to the grooves 114 and surface 110. Additionally, an adhesive can be applied in the grooves 114 and surface 110 prior to inserting the neck 111 into the distal end 71 of the tube 56. As yet another alternative, the neck 111 can be press-fit into the distal end 71 of the tube 56. The cutting portion 112 extends from the shaft 108, opposite the neck 110. The tip 92 is formed from a circular rod and includes a top surface 116 that slopes forward to the cutting portion 112 to provide the cutting portion 112 with a height less than the diameter H of the shaft 108. The width of the cutting portion 112 is smaller or equal to the diameter H of the shaft 108. The cutting portion 112 and a portion of the shaft 108 define a cutting opening 118 that is generally rectangular in shape. The neck 110 and shaft 108 define a cable opening 120 that extends into the cutting opening 118 to form a single continuous tip chamber 122. The cutting opening 118, proximate a front 124 of the tip 92, defines a front curved surface 126. The cutting opening 118, proximate the neck 110 and the cable opening 120, defines a rear curved surface 128. A hip 130 is formed on the rear curved surface 128, along the bottom of the tip 92 for providing a stop for the shoulder 80 of the cable 70.

The shaft 108, proximate the cutting portion 112, also defines a tip pin hole 82 that extends though the shaft 108 and the hollow interior 59. The blade end 74 of the cable 70 is inserted into the hollow interior 59 and the cable pin holes 83 of the cable 70 and the blade 90 are aligned. Additionally, the tip pin holes 82 of the blade 90 and the tip 92 are aligned. The blade 90 is assembled to the blade end 74 and a cable pin 132 is inserted through the aligned cable pin hole 83 to pivotally connect the blade 90 to the cable 70. Likewise, the blade 90 is assembled to the tip 92 by inserting the blade 90 within the hollow interior 59 between the tip pin holes 82 of the tip 92 and a tip pin 133 is inserted through the aligned tip pin holes 82 to pivotally connect the blade 90 to the tip 92. Because the tip 92 is connected directly to the tube 56, the tip 92 remains stationary. When the handles 48, 50 are moved relative to one another, the blade end 74 is moved fore/aft inside the hollow interior 59, by virtue of sliding the cable 70 inside the tube 56, the cable pin hole 83 slides fore/aft relative to the tip pin hole 82, which remains stationary. Therefore, the movement of the cable pin hole 83, relative to the fixed tip pin hole 82, causes the blade 90 to pivot about the tip pin 133 while moving the cutting member into and out of the hollow interior 59 of the tip 92. Movement of the cutting member relative to the cutting surface enables the cutting procedure to occur.

The body assembly 42, shown in FIG. 14, includes a body 134 and an arm 136 extending from the body 134. The body assembly 42 defines a passage 138 extending through the body 134 and the arm 136 along a common axis. The body 134 defines a chamber 140, which is circular, along the passage 138. The arm 136 defines a collet chamber 142, which is also circular, along the passage 138. The diameter of the collet chamber 142 is a smaller diameter than the diameter of the chamber 140 and extends to a threaded portion 143 and a locking nut 197. Rests 144 are formed on the outside of the arm 136 for providing a stop for each of the handles 48, 50. The body assembly 42 includes an upper surface 96 that defines a threaded hole 146 extending to an opening 148. The opening 148 extends between the threaded hole 146 and the chamber 140 on a locking axis BB.

A lock 150 is disposed in the opening 148. The lock 150 includes a base 152 that is sized to fit within the opening 148. A locking pin 154 depends from the base 152 for engaging a corresponding locking groove 62 on the tube assembly 46. A locking ramp 156 that slopes from near a top 158 of the base 152 toward the locking pin 154 is formed on opposite sides of the base 152. The body 134 also defines a locking hole 160 that intersects the opening 148. A spring cap 162 is threadedly engaged with the threaded hole 146. The spring cap 162 compresses and retains a spring 164 between the spring cap 162 and the lock 150 to bias the lock 150 toward the chamber 140. The spring cap 162 may define an orifice 199 for receiving a portion of the spring 164. Additionally, the lock 150 may define a spring pocket 159 for receiving a portion of the spring 164. The spring pocket 159 and the orifice 199 help to maintain the spring 164 in the position as it is compressed and released.

A release plunger 166, shown in FIGS. 15-18, includes a plunger shaft 168 disposed between a head 170 and an end 172. The plunger shaft 168 is disposed in the locking hole 160 along a plunger axis AA. The plunger shaft 168 is generally rod shaped and defines a slot 177 extending through the plunger shaft 168 and a plunger ramp 174, formed in the plunger shaft 168, adjacent and sloping toward the end 172. When the plunger 166 is disposed in the locking hole 160, the plunger ramp 174 opposes the locking ramp 156 and the locking ramp 156 imparts a force on the plunger ramp 174 along the locking axis BB. The locking ramp 156 and the plunger ramp 174 slope relative to the locking axis (lateral axis) BB, in opposite directions such that the plunger ramp 174 is opposed and slidable engages a surface of the locking ramp 156.

When the release plunger 166 is pushed along the plunger axis AA, toward the body 134, the plunger ramp 174 moves along the locking ramp 156 and pushes the lock 150 upward and away from the plunger 166, along the locking axis BB. When this happens, the locking pin 154 disengages the locking groove 62 of the tube assembly 46. When the locking pin 154 is disengaged from the locking groove 62, the tube assembly 46 is free to be rotated within the chamber 140 of the body 134 and align a different locking groove 62 with the locking pin 154. The tip assembly 60 rotates with the entire tube assembly 46 by virtue of the fixed connection between the tip assembly 60 and the tube 56 of the tube assembly 46. Therefore, if a different radial orientation of the tip assembly 60 is desired, relative to the body assembly 42 and handles 48, 50, the tube assembly 46 is rotated and locked into the preferred orientation via the locking pin 154. When the plunger 166 is released, the force imparted to the lock 150 from the locking spring 164 causes the locking pin 154 to automatically engage the locking groove 62.

To improve the ability of the surgeon to grip the body 134 to use the release plunger 166 to perform a one handed release of the tube assembly 46, a cap 173 is formed on the body 134, on the plunger axis AA opposite the head 170 of the release plunger 166, as shown in FIGS. 26 and 27. The cap 173 covers the end 172 of the release plunger 166 such that when surgeon grasps the body 134, a finger can rest on the cap 173 and another finger can rest on the head 170. This allows the surgeon to squeeze the head 170 along the plunger axis AA toward the cap 173 to release the locking pin 154 with a single hand.

An grabbing assembly 175 includes a collet 176 and a stem 178. The collet 176 includes a collet housing 180 and jaws 181 extending from the collet housing 180. The collet housing 180 is generally circular and defines a stem opening 182 for receiving a portion of the stem 178. The stem opening 182 extends through the collet housing 180 and into the jaws. The jaws 181 include two or more fingers 184 that extend from the collet housing 180 to be able to grab the cable end retainer 86. In a "relaxed" position, the fingers 184 diverge from the collet housing 180, as shown in FIGS. 29 and 31. When the fingers 184 are disposed inside of the collet chamber 142, the fingers 184 are "restricted" by the collet chamber 142 such that they extend from the collet housing 180 in a generally parallel relationship 130, as shown in FIGS. 28 and 30, and they grab and retain the cable end retainer 86 that is attached to the cable 70. When a tube assembly 46 is inserted into the body 134 and the fingers 184 are inside of the collet chamber 142, the cable end retainer 86 engages and retains the cable end 76 and is retained within the collet 176. The stem 178 includes a stem shaft 190 and a pair of stem arms 192, extending from the stem 178 in a spaced and parallel relationship. The stem arms 192 each define a stem hole 194, aligned along the same axis.

When the grabbing assembly 175 is disposed in the collet chamber 142, a resistance spring 195 surrounds the stem shaft 190, inside of the collet chamber 142. The resistance spring 195 is positioned between the collect housing 180 and the threaded nut 197. Accordingly, as the grabbing assembly 175 is pulled rearward in the collet chamber 142, the resistance spring 195 is compressed between the collect housing 180 and the threaded nut 197. When the grabbing assembly 175 is released, the resistance spring 195 forces the grabbing assembly 175 to slide forward in the collet chamber 142 and open handles 48, 50.

A top link 196 and a bottom link 198 are used to interconnect the stem 178 and the upper and the lower handles 48, 50. Each link defines a link hole 204 and a stem hole 194 at opposite ends thereof. Each handle 48, 50 defines a link hole 204. The top and the bottom links 198 are inserted between the arms of the stem 178 and the stem holes 194 of the top and the bottom links 198 are aligned with the stem holes 194 of the stem arms 192. A stem screw 208 is inserted through all of the stem holes 194 to retain the links 196, 198 to the stem arms 192, while allowing the links 196, 198 to pivot with respect to the handles 48, 50. The link hole 204 of the top link 196 is aligned with the link hole 204 of the upper handle 48. A link screw 200 is inserted through the link holes 204, while allowing the top link 196 to pivot with respect to the upper handle 48. The link hole 204 of the bottom link 198 is aligned with the link hole 204 of the lower handle 50. A link screw 200 is inserted through the link holes 204 while allowing the bottom link 198 to pivot with respect to the lower handle 50.

Figure 34:
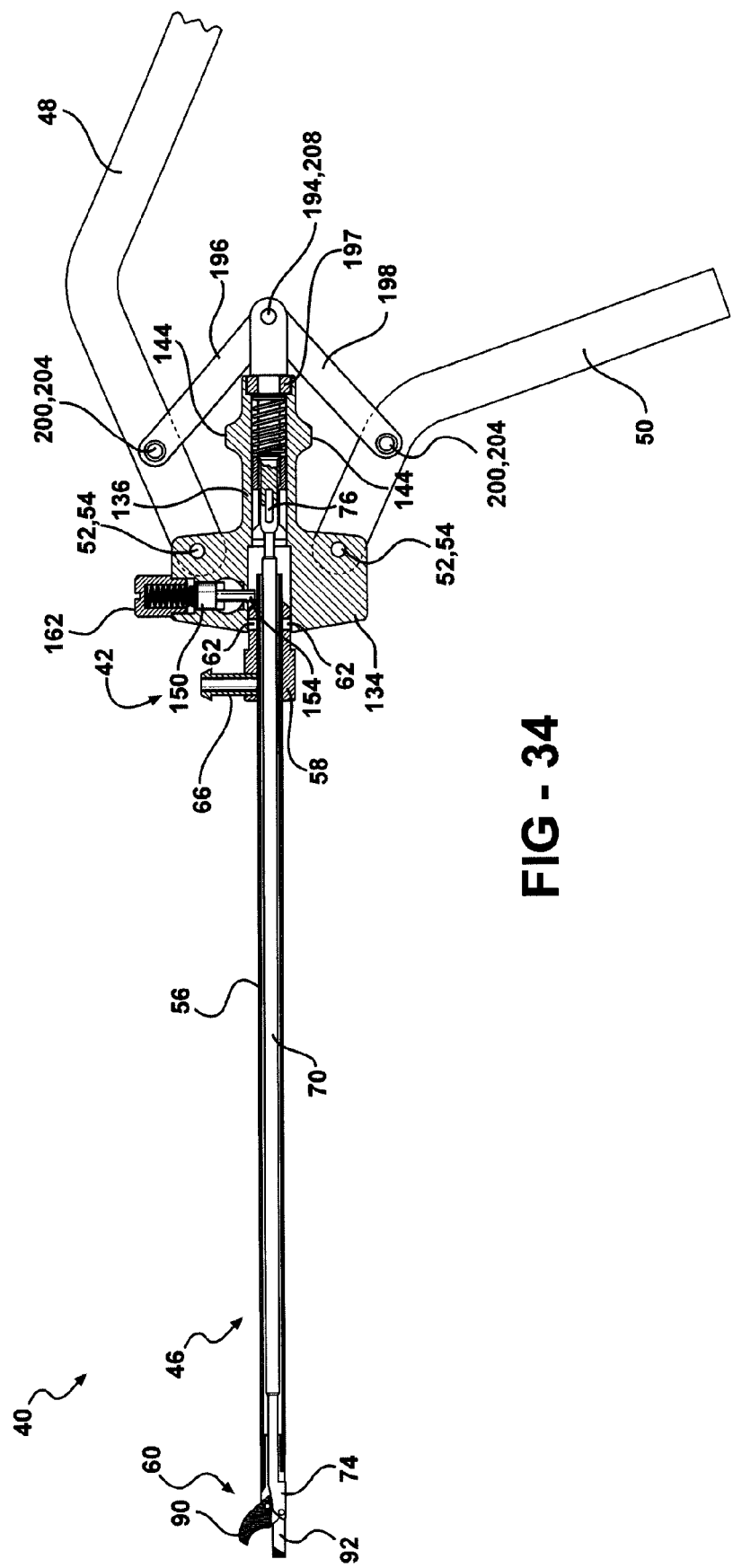
FIG. 34 is a partial cross-sectional side view of the forceps with the handles spread to the loading position for removing or inserting the tube assembly into the body assembly.

Referring to FIG. 34, loading and unloading a tube assembly 46 into the body assembly 42 is facilitated by spreading the upper and lower handles 48, 50 far apart, i.e., pulled apart from one another, such that the links 196, 198 cause the stem 178 to push the fingers 184 and cable end retainer 186 all the way into the body chamber 140, as shown in FIG. 34. When the fingers 184 and the cable end retainer 186 of the collet 176 enter the body chamber 140, the fingers 184 and cable end retainer 186 are no longer restricted by the collet chamber 142 and no longer engage the cable end 76, if a tube assembly 46 is already loaded into the body assembly 42. If the plunger 166 is also depressed and the locking pin 154 is no longer engaging the locking groove 62, the tube assembly 46 may be removed from the body assembly 42.

Figure 33:
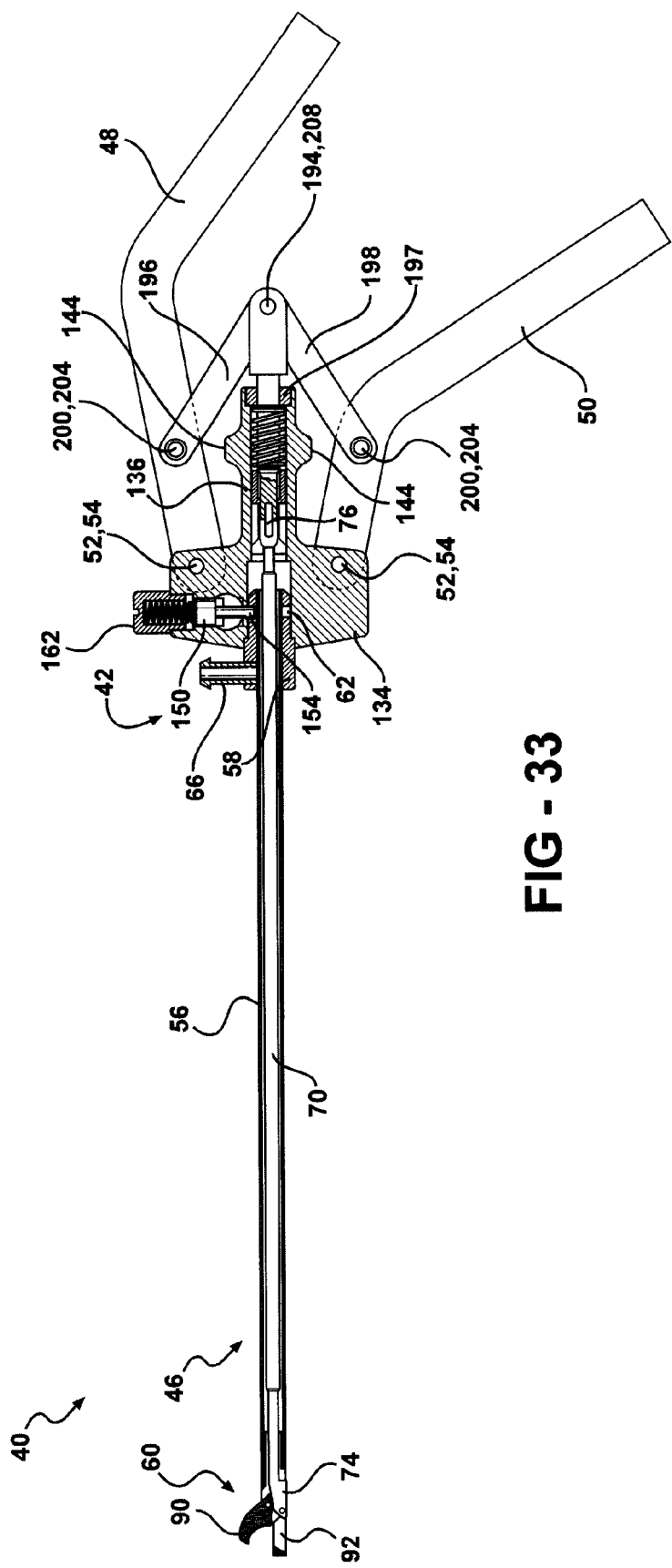
FIG. 33 is a partial cross-sectional side view of the forceps with the handles open and the blade of the tube assembly in the open position.

Referring to FIG. 33, as the upper and the lower handles 48, 50 are closed, i.e., pulled toward one another, the links 196, 198 cause the stem 178 to pull the fingers 184 and the cable end retainer 86 into the collet chamber 142. The slope 188 on each of the fingers 184 rides along a step 206 located between the chamber 140 of the body and the collet chamber 142. Because the diameter of the collet chamber 142 is smaller than the diameter of the chamber 140 of the body 134, the slope 188 and the step 206 cooperate to close the fingers 184 onto the cable end retainer 86. As the cable end retainer 186 is grabbed, it pulls the cable end 76 if a tube assembly 46 is inserted into the body assembly 42.

Figure 32:
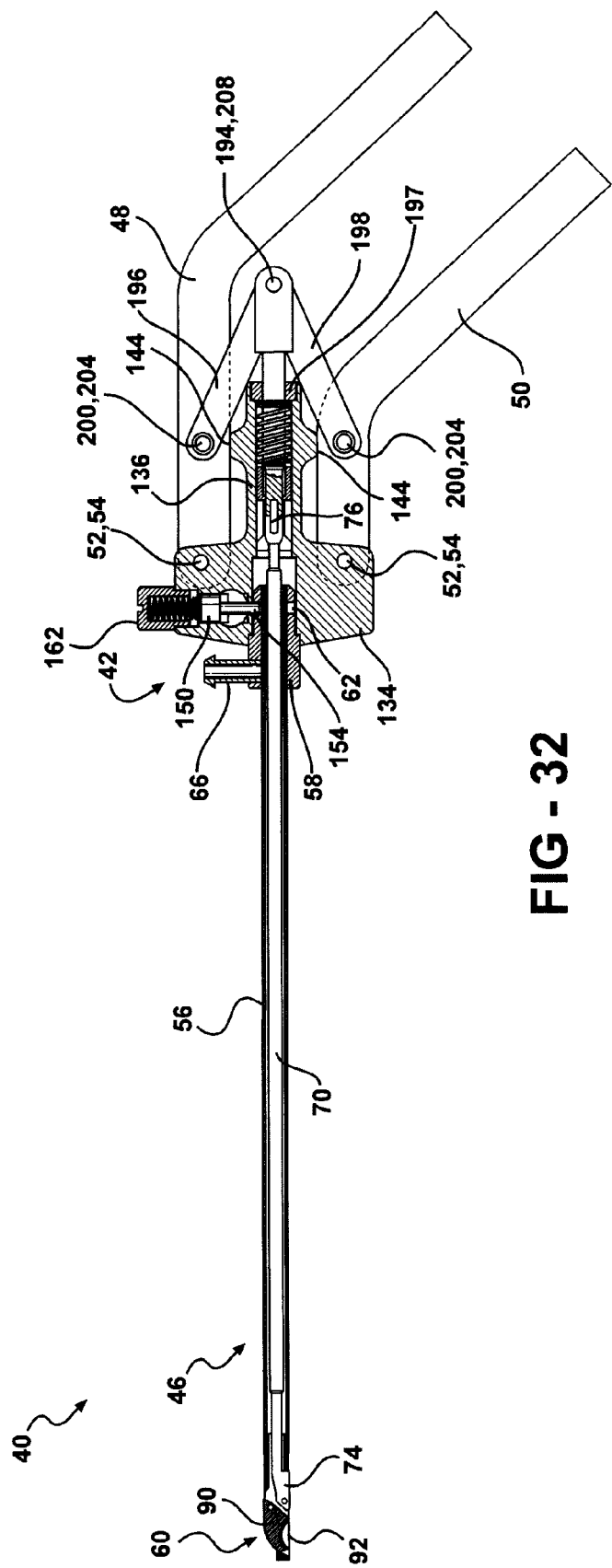
FIG. 32 is a partial cross-sectional side view of the forceps with handles closed and the blade of the tube assembly in the closed position.

Similarly, movement of the handles 48, 50 relative to one another moves the blade 90 relative to the tip 92 in the tip assembly 60. However, the handles 48, 50 are not spread as far apart as when loading and unloading a tube assembly 46 from the body assembly 42. Therefore, when the handles 48, 50 are moved apart, as shown in FIG. 33, the links 196, 198 cause the stem 178 to push the fingers 184 forward in the collet chamber 142 which, in turn, pushes the cable 70 forward through the tube 56. As the cable 70 moves forward in the tube 56, the cable end 76 and the blade 90, at the cable pin holes 83, slide forward in the tip assembly 60. However, because the blade 90 remains only pivotally connected to the tip 92 via the tip pinhole 82, the blade 90 rotates out of the hollow interior 59 of the tip 92. Likewise, as the handles 48, 50 are moved together, as shown in FIG. 32, the links 196, 198 cause the stem 178 to pull the fingers 184 rearward in the tube 56. As the cable 70 moves rearward in the tube 56, the cable end 76 and the blade 90, at the cable pinhole 83, slide rearward in the tip assembly 60. Accordingly, the blade 90 rotates into the hollow interior 59 of the tip 92 by pivoting about the tip pin 133.

There are four stops within the forceps 40 which operate to limit the rotation of the blade 90 with respect to the tip 92. First, as the handles 48, 50 are closed, stops 144 on the body assembly 42 limit the travel of the handles 48, 50 which limits the amount the blade 90 can enter the tip 92 of the tip assembly 60. Second, the hip 130 on the rear curved surface 128 of the tip 92 provides a stop for the shoulder 80 of the cable 70 to limit the travel of the blade 90 and prevent the cutting region 102 of the blade 90 from extending through the tip 92. Third, the front sloping edge 78 of the cable 70 cooperates with the first blade stop 107 to limit the travel of the blade 90 and limit the closing of the blade 90 with respect to the tip 92. The fourth included mechanical stop is when blade stop 109 on the blade 90 contacts the top edge 79 on the cable 70, as shown in FIG. 3, to limit the opening of the blade 90 with respect to the tip 92 to and angle CC usually no greater than 50 to 60 degrees, as shown in FIG. 3.

The shear pin 88 that retains the cable end 76 to the cable retainer 86 has a lower shear force than the tip pin 133 and the cable pin 132. This means that if too great of force is exerted on the entire tube assembly 46 by virtue of moving the handles 48, 50, the shear pin 88 will break and the tip pin 133 and the cable pin 132 will not. This is important because the shear pin 88 is inside of the chamber 140 of the body and will not result in any loose parts accidentally entering the patient during the surgical procedure should the shear pin 88 break.

Figure 35:
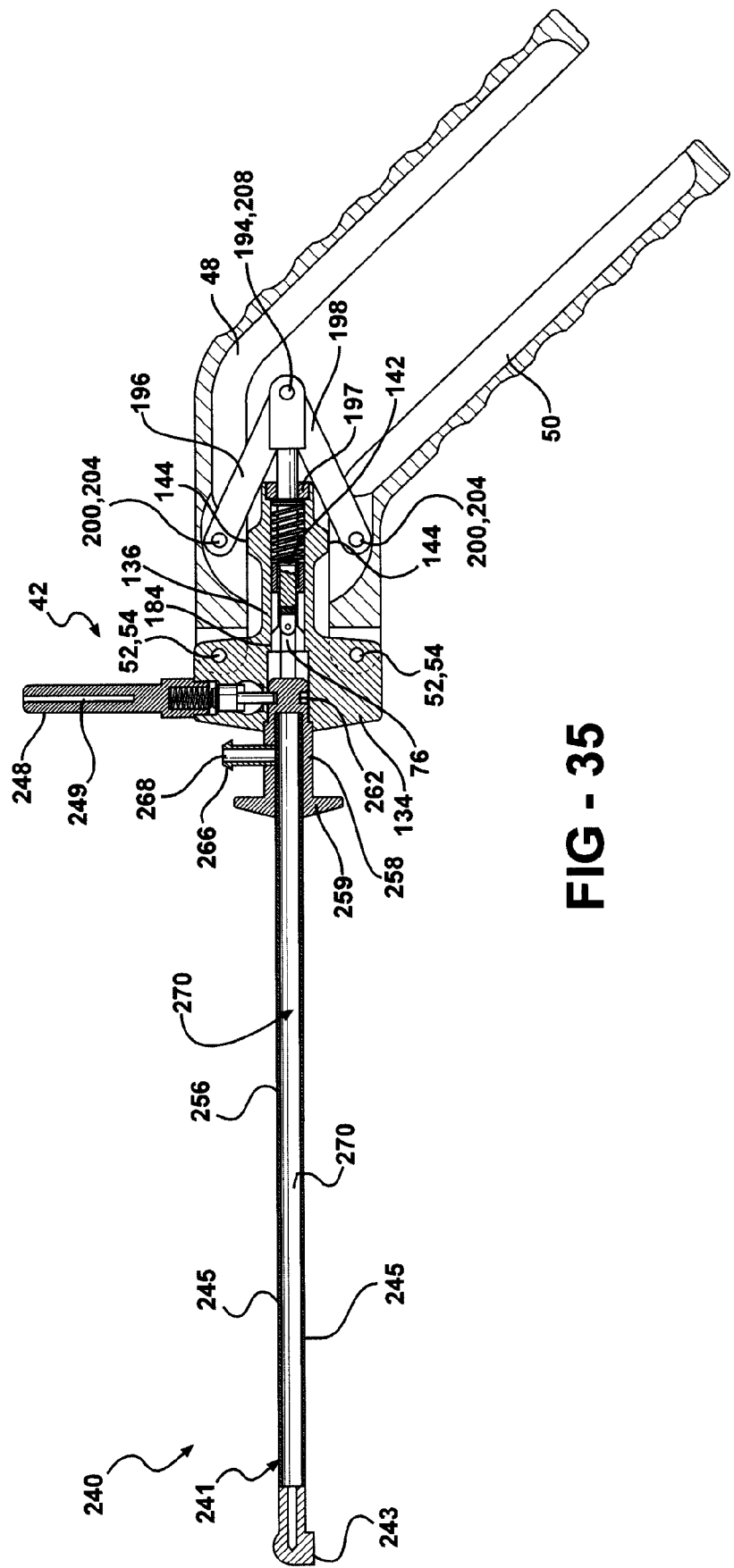
FIG. 35 is a cross-sectional side view of an alternative embodiment of the forceps showing an aspirating monopolar electrode inserted into the body assembly.
Figure 36:
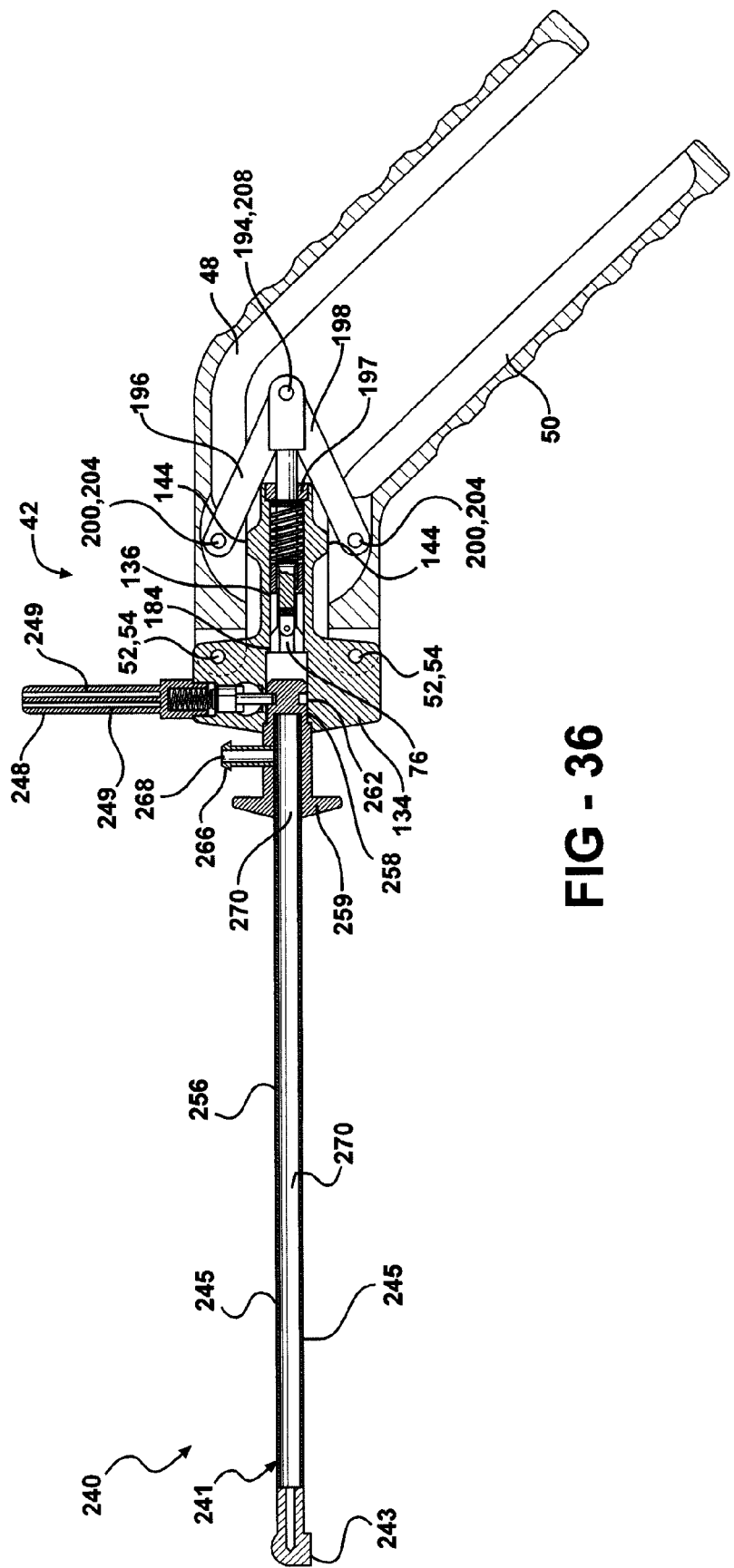
FIG. 36 is a cross-sectional side view of the alternative embodiment of the forceps from FIG. 35 showing an aspirating bipolar electrode inserted into the body assembly.

Referring to FIGS. 35 and 36, an alternative embodiment of the forceps 240 is shown. The forceps 240 are adapted to include an electrode assembly 241, such as an aspirating ablating electrode assembly 241, instead of the tube assembly 46. The electrode assembly 241 includes a hollow tube 256 extending between an adapter 258 and an ablating end 243. The adapter 258 encircles the tube 256 and defines a plurality of locking holes 262 and a groove 263 encircling the adapter 258. A knob 259 extends from the adapter 258 for being gripped to rotate the electrode assembly 241. The tube 256 and the adapter 258 each define a hollow interior 270. A flushing port 266 is formed in and extends from the adapter 258. The flushing port 266 defines a duct 268 into the hollow interior 270 of the adapter 258 for flushing the tube assembly 246, via pumping or sucking fluids from the area of the body the operation is occurring. At least one tube 256 extends between the ablating end 243 and the locking holes 262 and groove 263 of the adapter 258. When there is only one electrode 245, the electrode assembly 241 is a monopolar electrode assembly 241, as shown in FIG. 35. With the monopolar electrode assembly 241, a positive source of electricity is passed through the electrode 245 and a negative source of energy, or ground, is attached to a ground pad such that the energy passes through the patient and into the ground pad. This electricity can be used for cutting, sealing, ablation and coagulation.

However, when there are two sources of electricity energizing to tip 243, the electrode assembly 241 is a bipolar electrode assembly 241, as shown in FIG. 36. In the bipolar electrode assembly 241, power plug 248 takes the place of the spring cap 162 where the power plug 248 defines an internal shaft which provides a passage for the leads 249 to pass through the power plug 248 and into the body 134 to contact the adaptor 58 in two well separated spots. The leads 249 then extend to the electrode tip 243 where each lead charges individually insulated portions of the tip 243. Arcing between the insulated zones is used for bipolar cutting, sealing, ablation and coagulation. Additionally, to cool the electrodes 245, saline is passed through the flushing port 266, through the hollow tube 256, and out through or into the ablating end 243. The saline is required to provide efficient ablation of the tissue and to prevent the electrodes 245 from melting. Although saline is disclosed as a coolant, the invention is not limited to the use of saline as any other type of coolant may also be used so long as it provides sufficient cooling of the electrodes 245 and ablation of the tissue.

Figure 37:
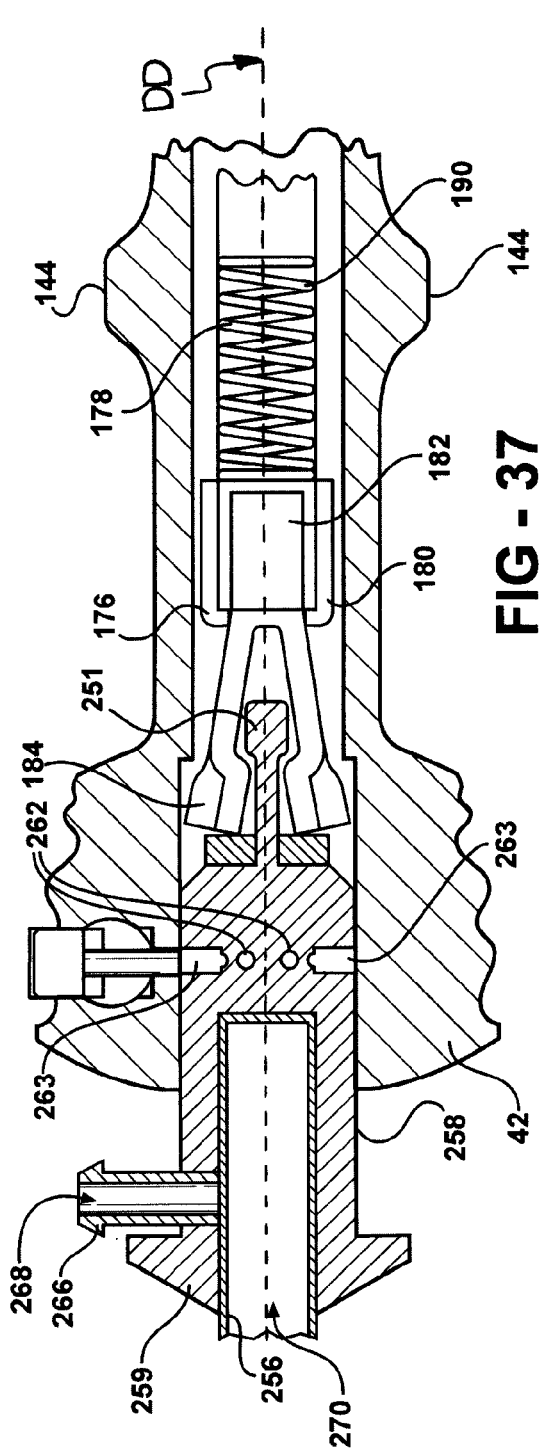
FIG. 37 is a partial cross-sectional side view of the alternative embodiment of the forceps showing fingers of the grabbing assembly and a column of the electrode inserted into the body assembly.
Figure 38:
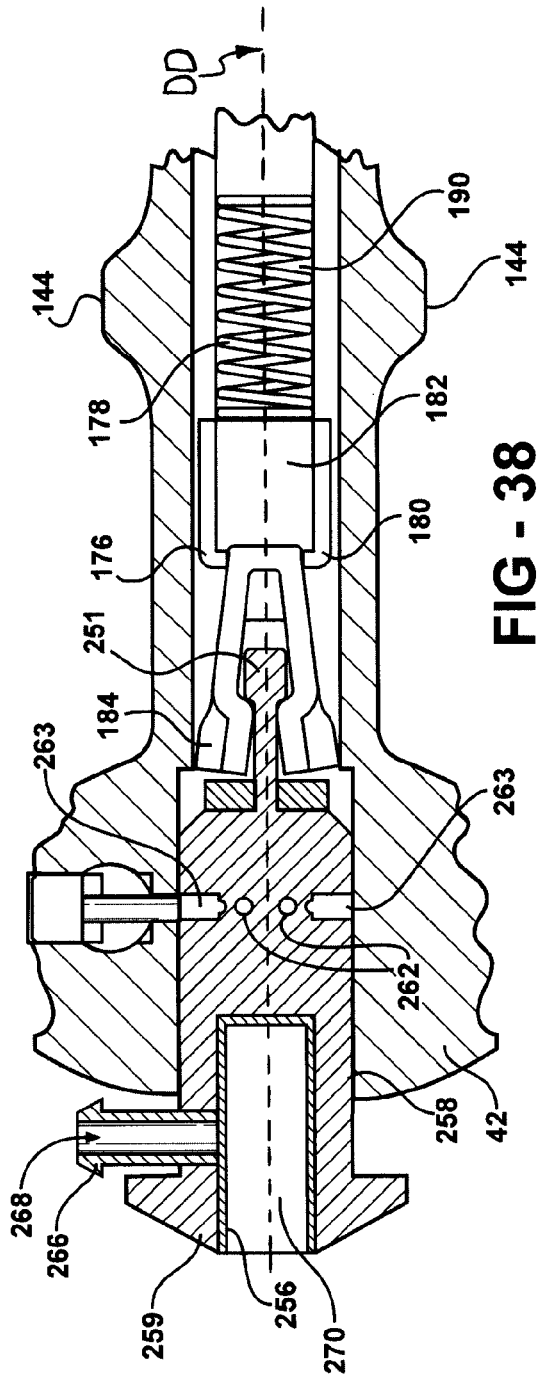
FIG. 38 is a partial cross-sectional side view of the alternative embodiment of the forceps showing the fingers of the grabbing assembly grasping the column of the electrode to retain the electrode in the body assembly.

As shown in FIGS. 37 and 38, when the electrode assembly 241 is used, articulation of handles 48, 50 is not required. Therefore, the electrode assembly 241 also includes an extension 251 which extends from the adapter 258 and simulates the cable end 86. To assemble the electrode assembly 241 to the body assembly 42, the handles 48, 50 are spread apart and in the open position. When the handles 48, 50 are in the open position, the links 196, 198 cause the stem 178 to push the fingers 184 forward in the collet chamber 142, as shown in FIG. 37. Then, the column 251 is inserted between the fingers 184 and the handles 48, 50 are closed. Closing the handles 48, 50 causes the stem 178 to pull the fingers 184 rearward in the collet chamber 142 and around the extension 251, as shown in FIG. 38. This, in effect, locks the electrode assembly 241 to the body assembly 42 and also keeps the handles 48, 50 immobile and enclosed so that the surgeon can grasp the handles 48, 50 to maneuver the electrode assembly 241 during surgery. To further insulate the surgeon from the energy going through the electrode assembly 241, the stem 178 and body 134 are formed from plastic or some other insulating type of material. However, the handles 48, 50 may be made from any type of metal or other type of non-insulating material because they are insulated from the electrode assembly 241 by the body made of or constructed by nonconductive material.

Figure 39:
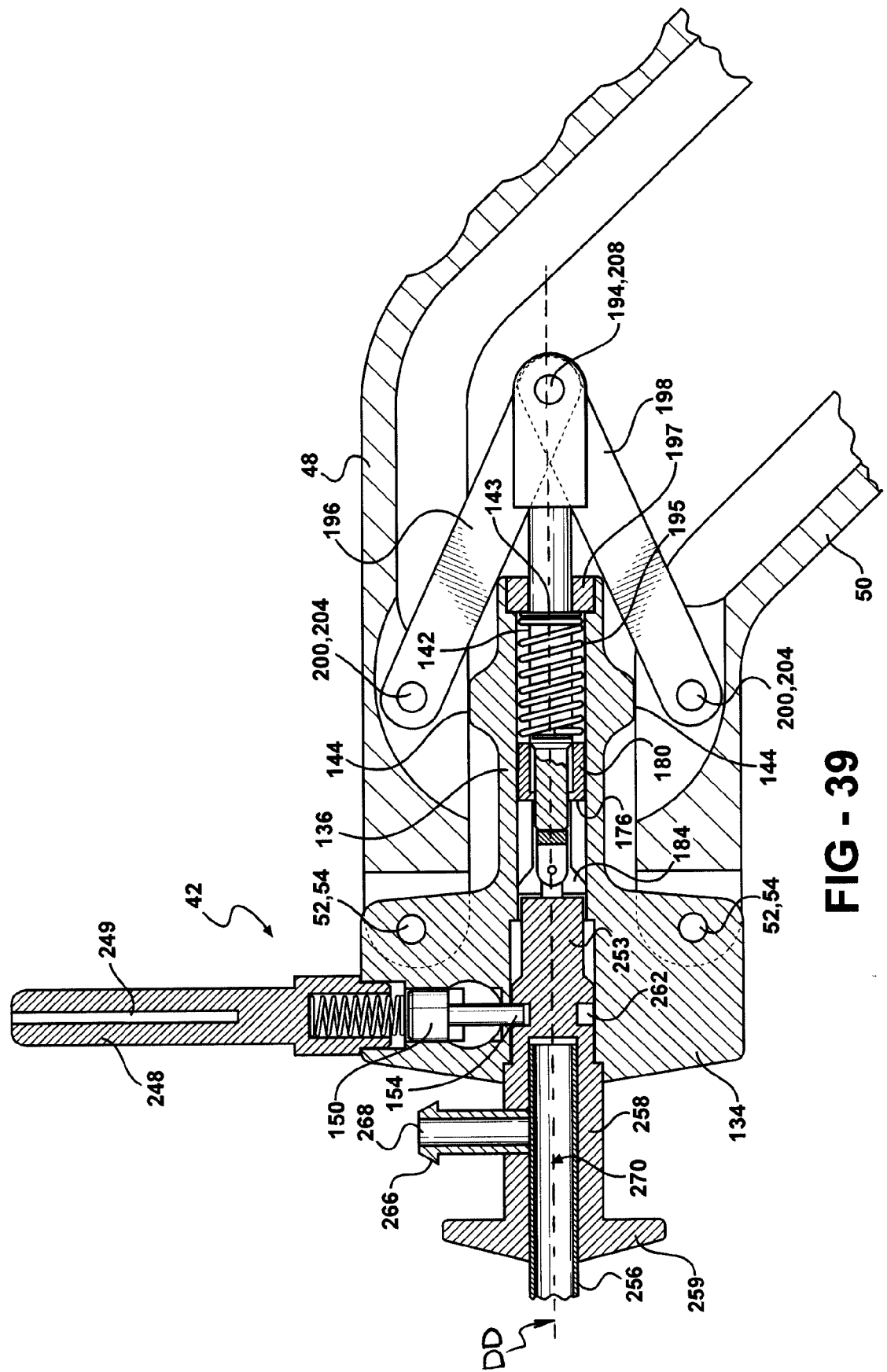
FIG. 39 is a partial cross-sectional side view of another alternative embodiment of the forceps showing an aspirating electrode inserted into the body assembly.

Alternatively, referring to FIG. 39, when the electrode assembly 241 is used the electrode assembly 241 also includes a trunk 253 which extends from the adapter 258 at a diameter at least slightly less than the diameter of the collet chamber 142. To assemble the electrode assembly 241 to the body assembly 42, the handles 48, 50 are spread apart and in the open position. When the handles 48, 50 are in the open position, the links 196, 198 cause the stem 178 to push the fingers 184 forward in the collet chamber 142. As the electrode assembly 241 is inserted into the body assembly 42, the trunk 253 pushes against the fingers 184 forcing the fingers 184 into the collet chamber 142 as the trunk 253 also enters the collet chamber 142. This also causes the handles 48, 50 to close. The electrode assembly 241 is locked into the body assembly 42 by virtue of the locking pin 154 engaging the locking groove 262 of the electrode assembly 241.

Many modifications and variations of the present invention are possible in light of the above teachings. In addition, the reference numerals in the claims are merely for convenience and are not to be read in any way as limiting.

What is claimed is:

1. A body assembly (42) of surgical forceps (40) for retaining an adapter (58) of a tube assembly (46) having a plurality of locking grooves (62) defined circularly around the tube assembly (46), said body assembly (42) comprising;
a housing (134) having an axial bore (140) with a circular cross section,
said housing (134) including a top surface (96) with said top surface (96) defining a transverse bore (148) extending along a locking axis (BB) and opening to said axial bore (140),
said housing (134) defining a lateral bore (160) extending along a plunger axis (AA) with said lateral bore (160) intersecting said transverse bore (148),
a lock (150) disposed in said transverse bore (148) and including a locking contact (156), and a locking pin (154) spaced axially from said locking contact (156), said locking pin (154) engagable with one of the locking grooves (62), and
a plunger (166) including a plunger shaft (168) with said plunger shaft (168) disposed in said lateral bore (160) and intersecting said transverse bore (148),
said plunger shaft (168) including a plunger ramp (174) sloping relative to said plunger axis (AA) and slidably interfacing with said locking contact (156) of said lock (150), wherein said plunger shaft (168) imparts a force on said locking contact (156) when said plunger (166) is pushed along said plunger axis (AA) to thereby move said locking pin (154) along said locking axis (BB) and disengage said locking pin (154) from the locking groove (62) and allow the tube assembly (46) to be rotated within the axial bore (140), and
said plunger shaft (168) defining a slot (177) wherein said locking pin (154) of said lock (150) extends through said slot (177).

2. A body assembly (42) as set forth in claim 1 wherein said locking contact (156) is further defined as a locking ramp (156) sloping relative to said locking axis (BB) in opposition to said plunger ramp (174) with said plunger ramp (174) and said locking ramp (156) slidably interfacing.

3. A body assembly (42) as set forth in claim 2 wherein said locking ramp (156) slopes at a first angle relative to said locking axis (BB) and said plunger ramp (174) slopes at a second angle relative to said locking axis (BB).

4. A body assembly (42) as set forth in claim 3 wherein said first angle and said second angle are equal and said locking ramp (156) includes a locking ramp (156) surface and said plunger ramp (174) includes a plunger ramp (174) surface with said surfaces in sliding contact.

5. A body assembly (42) as set forth in claim 1 wherein said lock (150) further includes a base (152) with said base (152) movably extending through said slot (177) and said locking pin (154) and said locking contact (156) positioned on opposite sides of said plunger shaft (168).

6. A body assembly (42) as set forth in claim 1 wherein said plunger ramp (174) is further defined as being formed in said plunger shaft (168) to define a V-shaped notch.

7. A body assembly (42) as set forth in claim 6 wherein said plunger ramp (174) is further defined as a pair of plunger ramps (174) formed in said plunger shaft (168) on opposing sides of said slot (177) in parallel.

8. A body assembly (42) as set forth in claim 7 wherein said locking contact (156) is further defined as a pair of locking contacts (156) for slidably interfacing with said corresponding plunger ramp (174).

9. A body assembly (42) as set forth in claim 8 wherein said locking contacts (156) are further defined as a pair of locking ramps (156) sloping in parallel relative to said locking axis (BB) and in opposition to said plunger ramps (174).

10. A body assembly (42) as set forth in claim 1 wherein said transverse bore (148) and said lateral bore (160) are generally perpendicular.

11. A body assembly (42) as set forth in claim 1 wherein said transverse bore (148) and said axial bore (140) are generally perpendicular.

12. A body assembly (42) as set forth in claim 1 wherein said plunger (166) further includes a head (170) extending from said plunger shaft (168) for pushing said head (170) to move said plunger (166) along said plunger axis (AA).

13. A body assembly (42) as set forth in claim 1 further including a spring cap (162) attached to said top surface (96) of said body covering said transverse bore (148) to retain said lock (150) within said transverse bore (148).

14. A body assembly (42) as set forth in claim 13 wherein said spring cap (162) further includes an electrode (249) for connection to an external power supply with said electrode (249) contacting said lock (150) to transmit current through said locking pin (154) and into the tube assembly (46).

15. A body assembly (42) as set forth in claim 14 further including a second electrode (249) for transmitting bipolar current through said locking pin (154) and into the tube assembly (46).

16. A body assembly (42) as set forth in claim 13 further including a spring disposed between said spring cap (162) and said lock (150) with said spring imparting a force on said lock (150) along said locking axis (BB) to bias said locking pin (154) into said axial bore (140) and provide resistance to said plunger (166) when moving said plunger (166) along said locking axis (AA).

17. A body assembly (42) as set forth in claim 16 wherein said lock (150) defines a spring pocket (159) opposite said locking pin (154) with a portion of said spring seated in said spring pocket (159) for nesting said spring within said lock.

18. A body assembly (42) as set forth in claim 16 wherein said spring cap (162) defines an orifice (199) with a portion of said spring seated in said orifice (199) for nesting said spring within said spring cap (162).

19. A body assembly (42) as set forth in claim 1 wherein said plunger (166) further includes an end (172) with a screw cap (179) disposed on said end (172) for retaining said plunger (166) within said lateral bore (160).

20. A body assembly (42) as set forth in claim 1 further including a cap (173) extending from said body and covering said lateral bore (160) for grasping said body assembly (42) and moving said plunger (166) along said locking with one hand.

21. A body assembly (42) as set forth in claim 1 wherein said body is formed from insulating material to isolate said body from an electrical current.

22. A body assembly (42) as set forth in claim 1 further comprising a tip assembly for attachment to said body assembly (42), said tip assembly including;

a shaft (108) defining a cable opening (120) with said cable opening (120) extending along a tube axis (DD), said shaft (108) defining a tip chamber (122) extending through said shaft (108) and intersecting said cable opening (120) with said shaft (108) including a hip (130), a blade (90) pivotally attached to said shaft (108) for performing a cutting operation, a cable (70) slidably disposed along said tube axis (DD) and extending into said cable opening (120) of said shaft (108) for sliding said cable (70) along said tube axis (DD) in said shaft (108), a cable end (74) extending from said cable (70) with said cable end (74) pivotally attached to said blade (90) for opening said blade (90) relative to said shaft (108) when said cable (70) is slid toward said blade (90) and closing said blade (90) relative to said shaft (108) when said cable (70) is slid away from said blade (90), a shoulder (80) protruding from said cable end (74) for limiting travel of said cable (70) as said cable (70) is moved along said tube axis (DD), said cable end (74) including a front sloping edge (78) and a top edge (79) sloping relative to said front sloping edge (78), said blade (90) including a first blade stop (107) and a second blade stop (107) sloped relative to said first blade stop (107) with said first blade stop (107) disposed against said front sloping edge (78) when said cable (70) is slid away from said blade (90) and said second blade stop (107) disposed against said top edge (79) when said cable (70) is slid toward said blade (90) to limit rotational travel of said blade (90) relative to said shaft (108).

\* \* \* \* \*